United States Patent
Paradis

[19]

[11] Patent Number: 6,079,432
[45] Date of Patent: Jun. 27, 2000

[54] CONTROL OF FLUID FLOW BY OVAL SHAPED VALVE MEMBER CONTAINING A CAM INTERFACE

[76] Inventor: Joseph R. Paradis, P.O. Box 22238, Hltn Hd Is., S.C. 29925

[21] Appl. No.: 08/674,435

[22] Filed: Jul. 2, 1996

[51] Int. Cl.⁷ ..................................................... A61M 5/00
[52] U.S. Cl. ........................... 137/1; 251/149.1; 604/167; 604/256
[58] Field of Search ................... 251/149.1, 251, 251/252; 604/256, 167, 169, 283, 249, 246, 86; 137/1

[56] References Cited

U.S. PATENT DOCUMENTS

| | | | |
|---|---|---|---|
| 3,853,127 | 12/1974 | Spademan | 604/167 |
| 5,279,571 | 1/1994 | Larkin | 604/256 X |
| 5,354,275 | 10/1994 | Behnke et al. | 604/256 X |
| 5,402,982 | 4/1995 | Atkinson et al. | 251/149.1 |
| 5,409,463 | 4/1995 | Thomas et al. | 604/167 |
| 5,549,577 | 8/1996 | Siegel et al. | 251/149.1 X |
| 5,676,346 | 10/1997 | Leinsing | 251/149.1 |
| 5,807,348 | 9/1998 | Zinger et al. | 604/283 X |
| 5,814,024 | 9/1998 | Thompson et al. | 604/256 X |

*Primary Examiner*—Kevin Lee
*Attorney, Agent, or Firm*—George E. Kersey, Esq.

[57] ABSTRACT

A flow control device with an inlet for fluid and a slit movable member having an oval shape before sealing the inlet at a cam interface and closing the slit. The unsealing of the inlet and the opening of the slit permits the passage of fluid therethrough. The movable member extends by a channel, which can be open or closed, between the inlet and an outlet and has a portion which is expandable laterally. A member external to the flow control device, such as the tip of a Luer taper, can activate the moveable member by depressing it to open the slit and allow the flow of fluid.

17 Claims, 6 Drawing Sheets

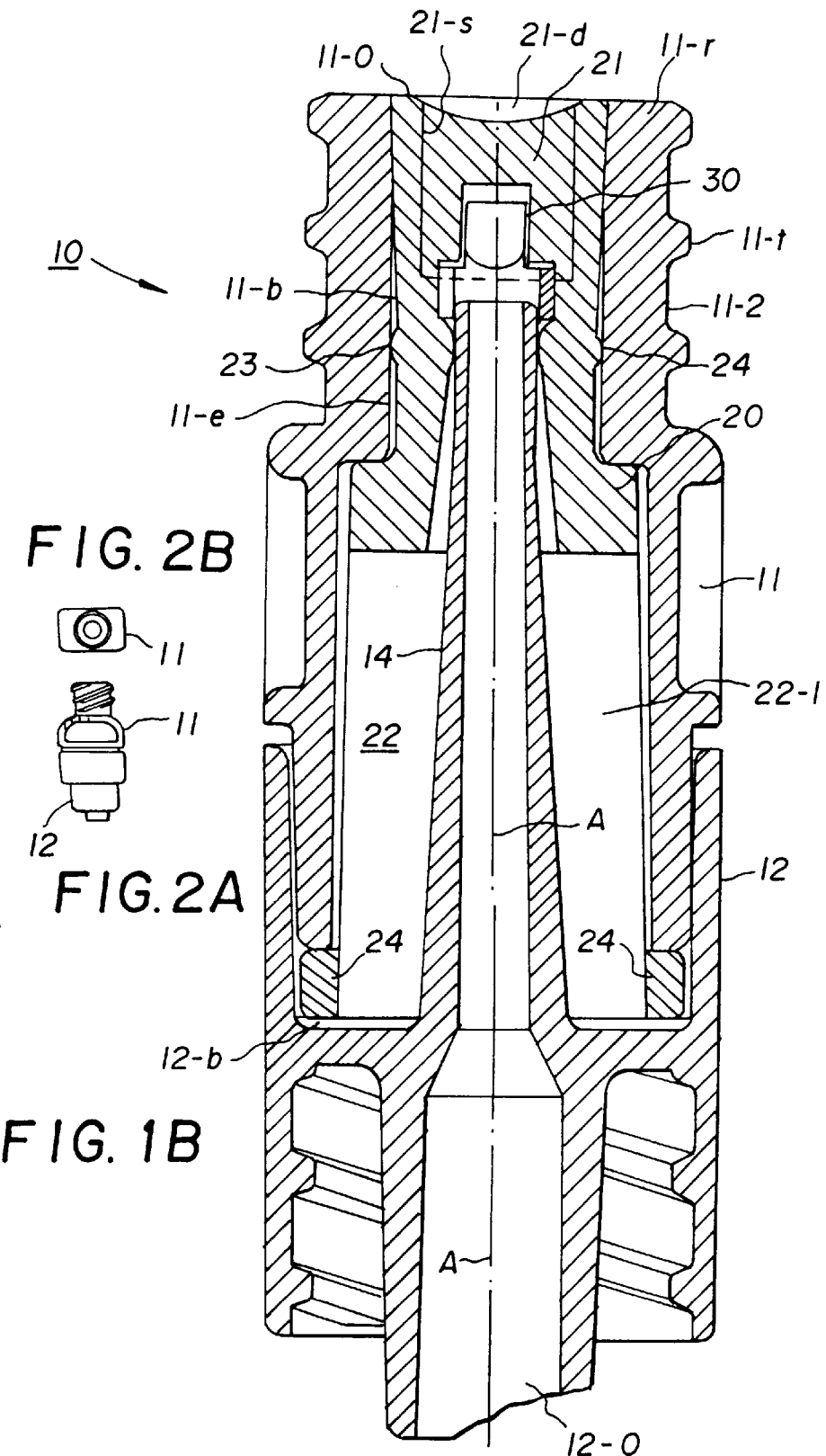

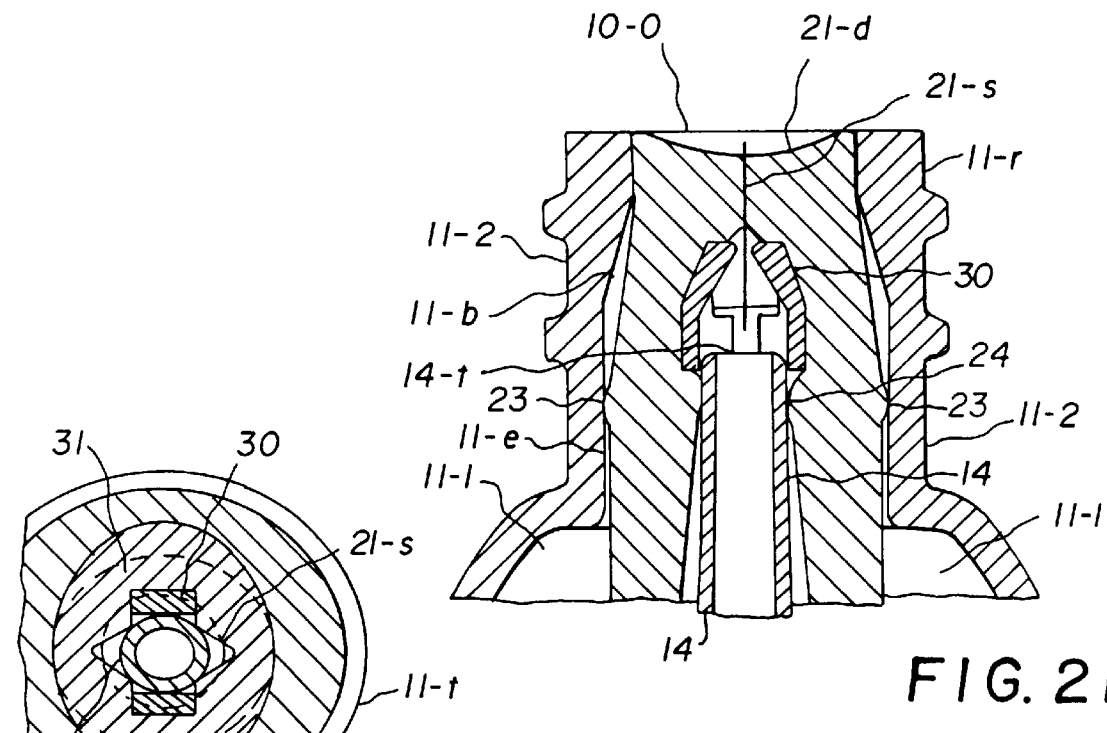
FIG. 2C
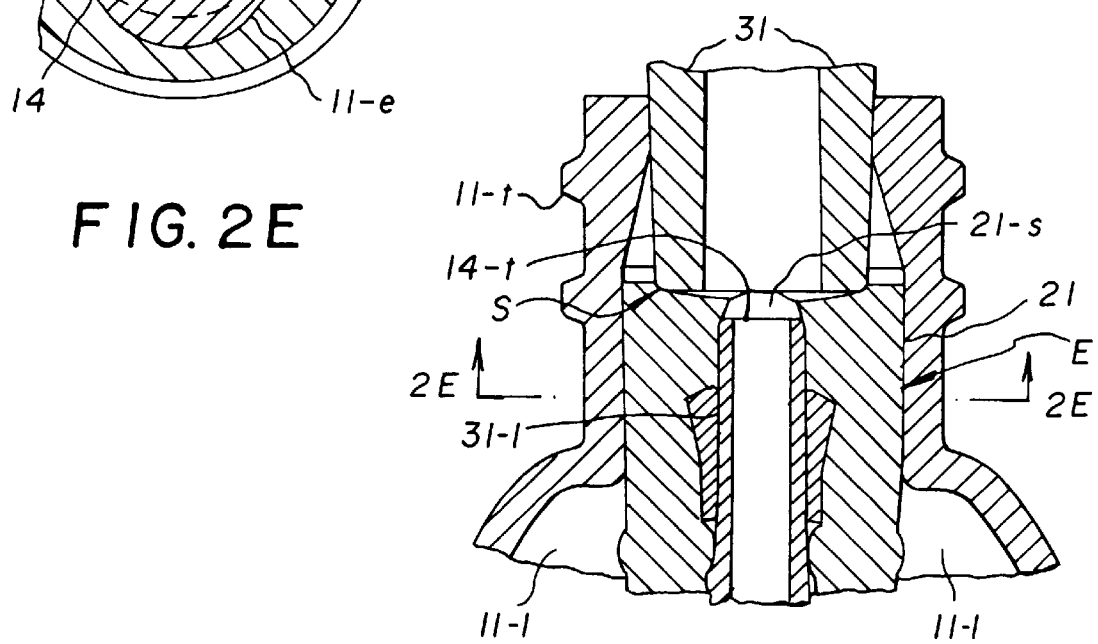
FIG. 2E
FIG. 2D

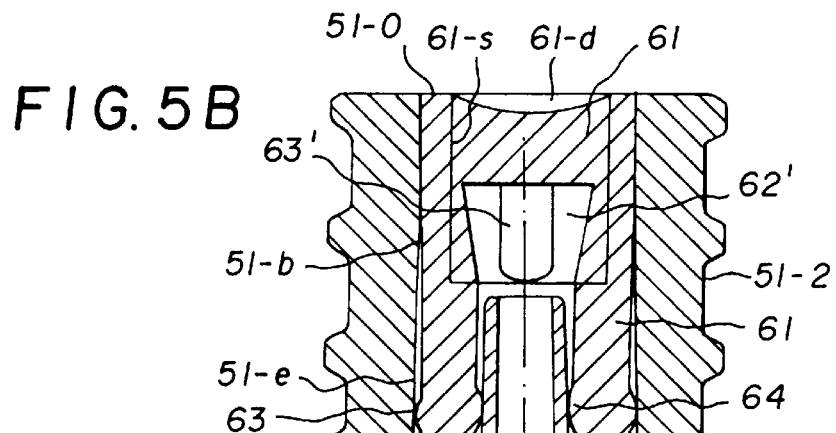
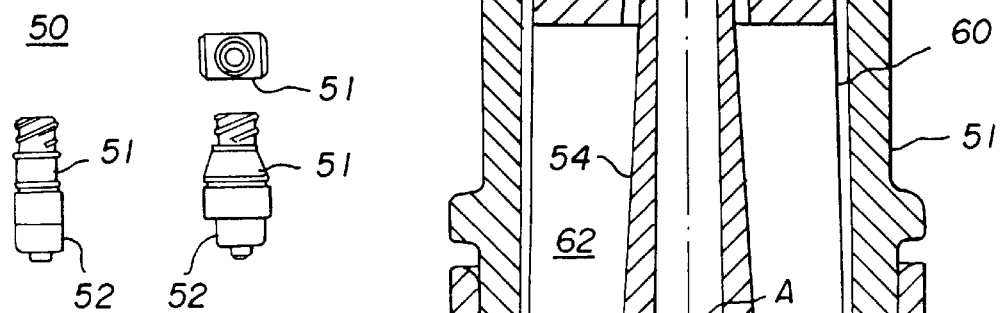
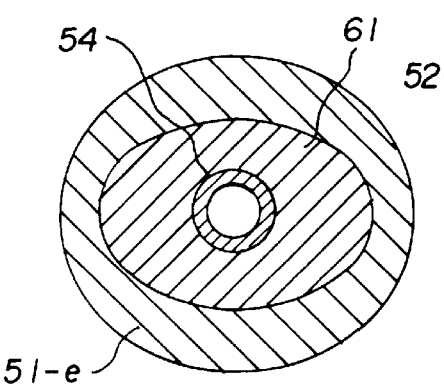
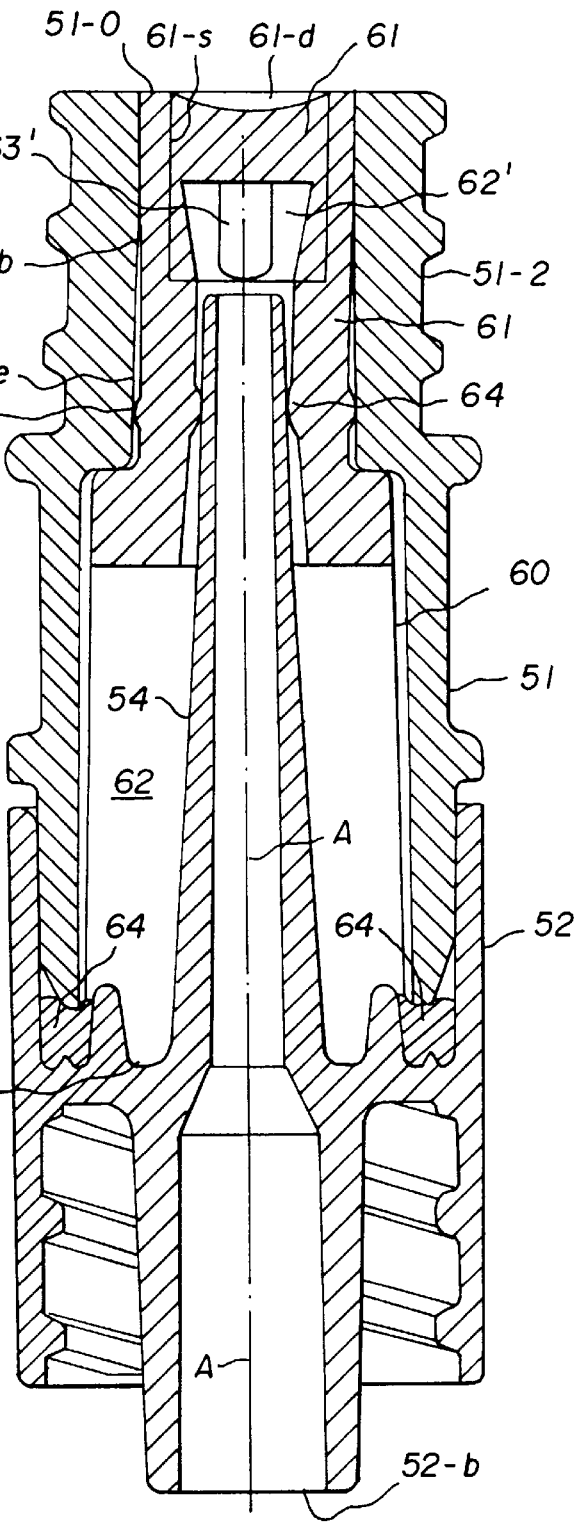

CONTROL OF FLUID FLOW BY OVAL SHAPED VALVE MEMBER CONTAINING A CAM INTERFACE

BACKGROUND OF THE INVENTION

This invention relates to flow control and more particularly, to the control of fluid flow with respect to the infusion and aspiration of fluids in venous and arterial systems.

A common container for medical fluids is a plastic pouch which contains saline, i.e. a salt solution used in biological and physiological processes. The contents of such a container are carried by a conduit, typically plastic tubing, through a valve that is used to prevent backflow.

In addition, other valves can be used with the conduit to provide for the infusion and/or aspiration of other substances, such as medicaments, body fluids, and anesthetics. Infusion is commonly used to introduce saline or other medical fluids into veins, while aspiration is commonly used to draw fluids from body cavities.

The ordinary valve used with conduits from medicinal containers functions by the deflection of an elastomeric element towards and away from a valve seat. The deflection is towards the valve seat in order to prevent flow, and away from the seat to permit flow.

In some cases the control of fluid flow is with respect to a multiplicity of channels that have varying degrees of convergence with one another. A typical multichannel arrangement makes use of connectors which permit the intercoupling of flow channels. For example, when two channels are to be joined to permit a common output, the connector can take the form of a fitting that resembles a "Y". When one of the channels terminates in an infusion site, the prior practice has been to access the site by needles, which are undesirable.

Because of the desirability of achieving needleless injection and infusion of fluids, there have been numerous attempts to achieve a satisfactory device. One such effort is disclosed in Rogers et al. U.S. Pat. No. 5,006,114 of Apr. 9, 1991 in which a valve assembly has a Luer lock on an inlet, and a movable piston seals the inlet.

When a syringe is attached to the Rogers inlet the piston is displaced to unseal a fluid channel which connects the end of the syringe to an outlet, and then to a device connected to a patient. When the syringe is removed from the inlet the piston is moved to its original closed position by an internal spring. This device suffers from the disadvantage that the spring acting against the piston results in a force against the inserted Luer tip that increases as the piston is displaced.

In addition, the Rogers valve assembly provides an outlet channel at an angle in relation to the inlet. As a consequence, it is difficult to manufacture the device, and there is a tendency for flash to accumulate at the entrance of the outlet channel in the vicinity of the piston.

Moreover, the Rogers design is intended for a Luer fitting which does not have a taper so that when the conventional tapered Luer fitting is employed, it can become jammed in the straight line walls of the inlet.

An attempt to overcome the disadvantages of Rogers is disclosed in Raines, U.S. Pat. No. 5,147,333, which issued Sep. 15, 1992. Raines accommodates a tapered Luer, but there is the continued disadvantage of the need for a spring to urge a piston or spool forwardly during closure of the valve and rearwardly when the valve is being opened.

As a result, the disadvantageous increase in spring force with displacement continues to be present. Furthermore, Raines has a "backcheck" valve which requires a pair of vertically offset ports that extend laterally from a tubular body, and a spool or piston is disposed between the ports. In addition, like the Rogers' predecessor, the piston or spool in Raines requires at least one projection from the end of the piston contacted by a Luer tip in order to permit the flow of fluid from the tip through the valve.

Furthermore, like Rogers, Raines is subject to difficulties in manufacture because of flash since the various outlet ports are angularly, i.e., perpendicularly, oriented in relation to their inlets.

Other techniques for the needleless infusion and aspiration of fluids are disclosed in my co-pending application Ser. No. 08/135,673, filed Oct. 13, 1993, now U.S. Pat. No. 5,509,433, issued Apr. 23, 1996, as well as in my other pending applications which are continuations-in-part of Ser. No. 08/135,673.

Accordingly, it is an object of the invention to achieve enhanced needleless injection, infusion and aspiration. A related object of the invention is to overcome disadvantages of the prior art.

A further object of the invention to enhance the control that can be achieved over fluid flow. A related object is to enhance flow control where fluid infusion or combination is to take place.

An important object of the invention is to eliminate the need for needle usage at injection sites. A related object is to maintain sterility at injection sites that are operated without needles.

An additional object of the invention is to improve the performance of valves for infusion, injection, aspiration and control of fluid flow.

A still further object of the invention is to achieve improved sealing pressure on components used in the infusion and aspiration of medicinal fluids.

SUMMARY OF THE INVENTION

In accomplishing the foregoing and related objects the invention provides a flow control device with an inlet for the flow of fluid; an outlet connected to the inlet and disposed to serve as a conduit for fluid flow, with the inlet having an oval, movable seal.

In accordance with one aspect of the invention, the moveable seal is slit and compressible, and can have an outer surface with a spherical or oval depression, so that the opening of a slit in the seal is facilitated and extrusion of material from the moveable seal in contact with an internal member seal is reduced during movement of the seal against the internal member.

The moveable seal desirably is oval to enhance sealing pressure at the circular inlet without the need for excess compression. This facilitates return of the moveable seal from an unsealed to a sealed position. A neck below the entrance of the inlet can have an oval interior to facilitate accommodation of the oval moveable seal.

The moveable seal has a neck extending from the entrance of the inlet with an oval ring to provide further sealing engagement in relation to the housing of the inlet.

In accordance with another aspect of the invention, the moveable seal contacts an internal member against which the moveable seal is depressed during operation of the device. A cam interface can be included within the moveable seal and be engageable by the internal member when the moveable seal is depressed.

In accordance with a further aspect of the invention, the moveable seal is elastomeric and the cam interface is fabricated of a material which has a greater hardness than the moveable seal. This avoids gouging of the elastomer of the seal by action of the internal member during operation of the device.

Independently of the cam interface, the moveable seal can have an interior cam surface for facilitating the movement of an internal member within the moveable seal during depression of the seal.

In accordance with still another aspect of the invention, the inlet extends to a first body portion containing the moveable seal; the outlet extends to a second body portion containing the moveable seal; and the first body portion is joined to the second body portion, for example, by interlocking of the two body portions.

The moveable seal can have a head extending to flexible legs and include a channel extending to the outlet for permitting flow through the head to the outlet when the inlet is unsealed. The outlet can extend to an internal bore member which is in engagement with the head of the movable seal and is spaced from the flexible legs, with an aperture of the head being opened when the head is moved along the bore member. The flexible body can be rectangular in cross-section and spaced from the bore member.

The movable seal can be activated by a member external to the flow control device, with the moveable seal terminating in an oval head sealing the inlet and depressible by an external member. The oval head can include a slit extending to an interior passageway within the head.

In a method of the invention for controlling fluid flow, the steps include: (1) sealing a circular inlet by an elliptically or oval-shaped flexible stopper with a slit that is maintained closed by compression at the inlet; and (2) depressing the stopper to open the slit and permit the flow of fluid therethrough. Further steps can include: (1) depressing the stopper by the tip of a Luer fitting; (2) depressing the stopper to cause its expansion and open the slit therein to permit the passage of fluid; (3) wiping an interior side wall extending from the inlet as the stopper is expanded during the depression thereof, and following the return of the stopper to its equilibrium position; (4) causing fluid to flow through a bore member to an outlet for the fluid; and (5) causing the bore member to open the slit of the stopper.

In a method of fabricating a flow control device, the steps include: (a) molding an inlet housing having a circular inlet and a neck with an elliptical or oval expansion region and a rectangular expansion chamber beyond the neck; (b) molding an outlet housing which complements the inlet housing; (c) inserting between the inlet and outlet housings, a compressible stopper having an elliptically or oval-shaped head extending to flexible legs; and (d) joining the inlet and outlet housings together.

The head of the stopper desirably is slit after compressive assembly within a circular entrance of the inlet housing. An internal channel of the head extends from the slit and can be adapted to receive a cam interface of harder material than the head to limit gouging of the head by an internal cannula, or the internal channel can be asymmetric below the slit, with oppositely diverging walls surfaces in orthogonal cross sections of the head.

DESCRIPTION OF THE DRAWINGS

FIG. 1A is a scale view of one side of a flow-control valve in accordance with the invention;

FIG. 1B is an enlarged sectional view of the flow-control valve of FIG. 1A in its closed valve position;

FIG. 2A is a scale view of another side of the flow-control valve of FIG. 1A.

FIG. 2B is a scale view of the top side of the flow-control valve of FIG. 2A;

FIG. 2C is an enlarged sectional view of the flow-control valve of FIG. 2A in its closed valve position;

FIG. 2D is an enlarged sectional view of the flow-control valve of FIG. 2A in its "operational flow" position with an external pressure member;

FIG. 2E is a sectional view of the flow-control valve of FIG. 2D taken along the lines D—D;

FIG. 5A is a scale view of one side of an alternative flow-control valve in accordance with the invention;

FIG. 5B is an enlarged sectional view of the flow-control valve of FIG. 5A in its closed valve position;

FIG. 6A is a scale view of another side of the flow-control valve of FIG. 5A.

FIG. 6B is a scale view of the top side of the alternative flow-control valve of FIG. 6A;

FIG. 6D is a sectional view of the flow-control valve of FIG. 6B taken along the lines C—C;

DETAILED DESCRIPTION

Figure 4C:
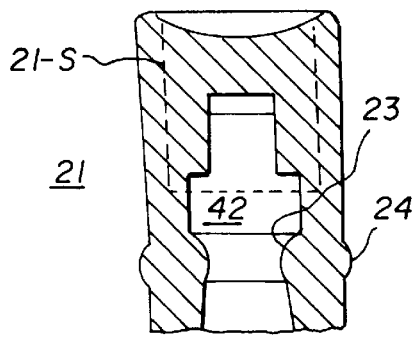
FIG. 4C is an elevational, lateral sectional view of the seal plug of FIG. 4A.

With reference to the drawings, FIG. 1A is a scale view of one side of a flow-control valve 10 in accordance with the invention. The valve 10 is rectangular in overall cross-section as indicated in FIG. 2B, with FIG. 1A showing the shorter side and FIG. 2A showing the longer side.

In the enlarged sectional view of FIG. 1B, the flow-control valve 10 of FIG. 1A is shown in its "pre-loaded" condition with an inlet opening 11-o of an inlet housing 11 sealed by the head 21 of a depressible plug 20. As indicated in FIG. 1B, the head 21 of the plug 20 has a slit 21-s, which is in closed compression. In addition, the valve 10 has an outlet housing 12 with an outlet opening 12-o. The outlet housing 12 is connected to the inlet housing 11 and disposed to serve as a conduit for the throughflow from the outlet opening 12-o of fluid that is applied at the inlet opening 11-o.

The depressible plug or movable seal 20 (as shown further in FIGS. 2C, 2D, 2E, 4A, 4B and 4C) has a flexible head 21 which seals the inlet 11-*o* and extends to a flexible body 22 for controlling flow by the outward flexing of the body 22 when the head 21 is depressed as indicated in FIG. 2D.

In effect, the plug 20 forms a seal with a hollow head 21 and a slotted body 22. The base of the body 22 terminates in a circumferential rectangular base 24. The rectangularity avoids twisting during any twisting that accompanies downward movement of a contacting element such as a Leur tip that engages the head 21.

In the flow control device 10, the movable plug 20, together with the head 21 and the flexible body 22, extends between the inlet opening 11-*o* and the outlet opening 12-*o*. The flexible body 22 is expandable laterally with respect to the vertical axis A of the outlet channel 12 in order to create spring pressure during opening and closing of the slit 21-*s*. Consequently, the upper or inlet housing 11 has an enlarged expansion chamber 11-1 as indicated in FIGS. 2C and 2D. In addition, the housing 11 has a neck 11-2 with exterior Luer threads 11-*t* and a tapered bore 11-*b* beyond an interior cylindrical rim 11-*r*. Extending from the tapered bore 11-*b* is an elliptical or oval bore 11-*e* which, in turn, extends to the expansion chamber 11-1.

An elliptical or oval-shaped O-ring 23 of the plug 20 engages the elliptical bore 11-*e*, and the head 21 seals the inlet rim 11-*r* by being compressed against its circular interior. The head 21 remains in sealing contact with the tapered bore 11-*b* of the neck 11-2, and then with the wall 11-*e*, as the plug 20 is depressed.

However, during movement of the plug 20 along the taper of the bore 11-*b*, the head 21 is depressed along an internal cannula 14 that extends upwardly from the base 12-*b* of the outlet housing 12 and the slit 21-*s* opens as shown in FIGS. 2D and 2E. Within the expansion chamber 11-1 legs of the flexible body 22 can be displaced to the chamber walls. For the embodiment of FIGS. 1B, 2C, 2D, 2E, 4A and 4C, the head 21 of the plug 20 has its upper slit 21-*s* within the spherical or oval concave depression 21-*d*, so that when a Luer tip, such as the tip 31 of FIG. 2D is threaded on the neck 11-2 it seals circumferentially as shown in FIG. 2D by the arrow S on top of plug 20 and there is no impediment to flow from the interior of the tip 31. The spherical or oval concavity 21-*d* on the top of the resilient seal plug 20 improves opening of the slit 21-*s* at the top of the seal plug head 21. It also helps to eliminate plug extrusion during valve activation by a Luer fitting or a syringe Luer outlet. The expansion of the head 21 as indicated by the arrow E in FIG. 2D also seals the neck 11-2 during valve operation.

The elliptical or oval shape of the resilient seal plug head 21 improves sealing pressure on the slit 21-*s* without the need for high compression. This configuration also allows high internal pressure, or low internal vacuum, without leakage and also achieves a desirably fast return of the seal plug head 21 to its sealing position within the rim 11-*r*, since there is reduced head compression of the seal plug.

The elliptical or oval shape of the internal neck 11-2 of the housing 11 below the Luer lock area, as indicated in FIG. 2D by the arrow E, further improves the performance of the primary seal. The internal elliptical or oval shape of the neck 11-2 corresponds to that of the seal plug head 21 when the cannula 14 moves through the resilient seal plug head along the slit 21-*s*. This is accomplished during valve opening because of pressure applied to the head 21 by a device such the Luer fitting 31 shown in FIG. 2D. The elliptical or oval shape of the internal neck 11-2 of the housing 11 additionally avoids a high degree of compression on the exterior wall of the internal blunt cannula 14. As a result, there is reduced interference that ensures a fluid seal at the elliptical interior of the neck 11-2 as well, as in the tapered region 11-*b* above the elliptical interior.

This reduction in interference permits a fast return of the head 21 of the seal plug 20 to its sealing position when the Luer fitting 31, or similar device, is removed following completion of valve activation.

In addition, the elliptical or oval shape of the O-ring 23 provides reduced interference in the neck region 11-2 of the housing 11 for a secondary seal which is desirable during the period of time that the valve 10 is in a fluid line, such as that of a IV set or vascular access system, and there is no activation with a Luer fitting or similar device. During this period, it is possible to have a high internal fluid pressure and the further seal of the circular O-ring 24 backs the pressure and avoids an internal pressure leak at the interface of the blunt cannula 14 and the internal circular O-ring seal or protuberance 24'.

The embodiment of FIGS. 1A through 4C is useful, for example, for relative low pressure infusion of fluids, e.g. by gravity flow from a saline bag (not shown). It is to be noted that because of the slit 21-*s*, pressure against the outer surface of the head 21 does not cause a collapse of material which could block the tip 31.

The Luer tip 31 thus permits activation of the control plug by a member external to the flow control device 10 since the plug 20 is seated in the inlet 11-*o* and can be depressed from its compressed seal position to the bore 11-*e*. In effect the control is by plug 20 with its upper head portion 21 sealing the inlet 11-*o*, and walls straddling the outlet cannula 14. The walls are extended legs of which only the leg 22-1 is visible in FIG. 1B. The legs, including leg 22-1, are bowed and flexed or buckled under pressure in the axial direction of the outlet channel 12-*o*. They extend from below the head 21 sealing the inlet 11-*o* to the base 12-*b* of the lower body 12 encircling the outlet channel cannula 14.

It is to be noted, as shown in FIGS. 1B through 2D, that the interior of the plug 20, which is desirably of an elastomeric material, can include a cam interface 30 which is of a relatively harder material, such as polypropylene. The cam interface 30 of FIGS. 1B through 2D is shown in detail in FIGS. 3A through 3D. Since the cam interface 30 engages the tip 14-*t* of the internal cannula 14 when the plug 20 is in its sealing position as shown in FIG. 2C, depression of the plug 20 causes the cannula 14 to contact the interior walls 31-1 and 31-2 of the interface cam 30 as the head slit 21-*s* is opened. As a result, gouging of the head 21 by the cannula 14 is avoided.

Figure 4A:
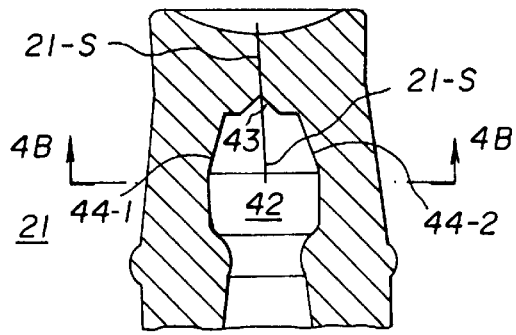
FIG. 4A is an elevational sectional view of the seal plug of FIG. 2C showing its interior before assembly of its cam interface.
Figure 4B:
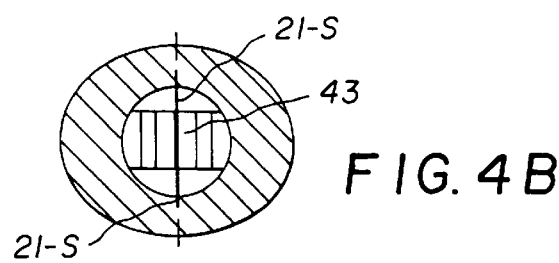
FIG. 4B is a sectional view of the seal plug of FIG. 4A taken along the lines C—C.

Details of the construction for the interface cam 30 are shown in FIGS. 3A through 3D, while details of the construction for the head 21 in order to accommodate the interface cam 30 are shown in FIGS. 4A through 4C.

Figure 3B:
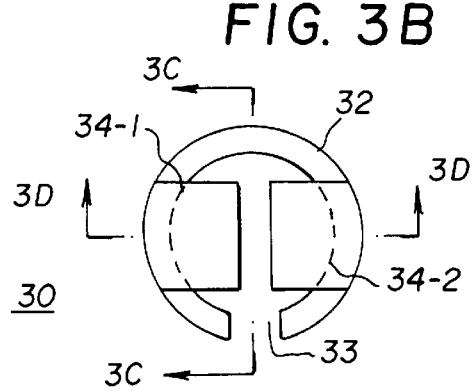
FIG. 3B is a top view of the cam interface in FIG. 3A.
Figure 3C:
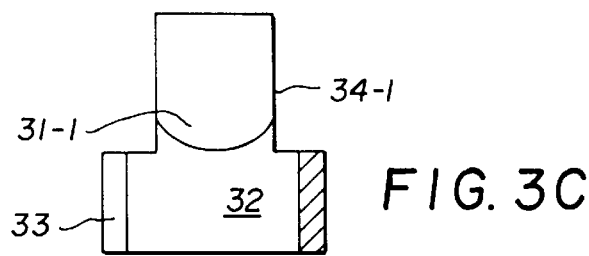
FIG. 3C is a sectional view of the cam interface of FIG. 3B taken along the lines B—B.
Figure 3A:
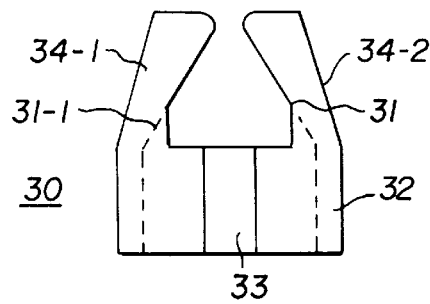
FIG. 3A is a elevational view of a cam interface shown for the valve of FIGS. 1B and 2C through 2E.
Figure 3D:
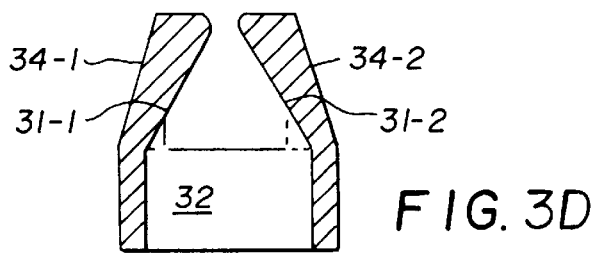
FIG. 3D is a sectional view of the cam interface of FIG. 3B taken along the lines A—A.

As seen in FIGS. 3A and 3B the interface cam 30 has a base ring 32 with a gap 33 and mounting cams 34-1 and 34-2, with respective cam walls 31-1 and 31-2. FIG. 3C is a sectional view of the cam interface 30 of FIG. 3B taken along the lines B—B showing half of the base ring 32 extending to the gap 33 and the cam surface 31-1 that engages the cannula 14. FIG. 3D is a sectional view of the cam interface 30 of FIG. 3B taken along the lines A—A showing the positioning of the cams 34-1 and 34-2 on the sectioned base ring 32.

As seen in FIGS. 4A and 4C the head 21 of the plug 20 has its interior below the slit 21-*s* proportioned to accommodate the interface cam 30 by having a base ring recess 42 and mounting cam surfaces 44-1 and 44-2. A V-notch 43 above the surfaces 44-1 and 44-2 is provided to enhance slit opening during operation. As indicated in FIG. 4B, the slit 21-*s* extends into the elliptical side walls of the head 21.

A further embodiment 50 of the invention is shown in FIGS. 5A through 6E. FIG. 5A is a scale view of one side of another flow-control valve 50 in accordance with the invention. Again, the valve 50 is rectangular in overall cross-section as indicated in FIG. 6B, with FIG. 5A showing the shorter side and FIG. 6A showing the longer side.

In the enlarged sectional view of FIG. 5B, the flow-control valve 50 of FIG. 5A is shown in its "pre-loaded" condition with an inlet opening 51-*o* of an inlet housing 51 sealed by the head 61 of a depressible plug 60. As indicated in FIG. 5B, the head 61 of the plug 60 has a slit 61-*s*, which is sealed due to compression. In addition, the valve 50 has an outlet housing 52 with an outlet opening 52-*o*. The outlet housing 52 is connected to the inlet housing 51 and disposed to serve as a conduit for the throughflow from the outlet opening 52-*o* of fluid that is applied at the inlet opening 51-*o*.

The depressible plug or movable seal 60 (as shown further in FIGS. 6C, 6D, 6E and 6F) has a flexible head 61 which seals the inlet 51-*o* and extends to a flexible body 62 for controlling flow by the outward flexing of the body 62 when the head 61 is depressed.

In effect, the plug 60 forms a seal with a hollow head 61 and a slotted body 62. The base 52-*b* of the housing 52 is circumferential and approximately rectangular to avoid turning during any twisting that accompanies downward movement of a contacting element that engages the head 61.

Figure 6C:
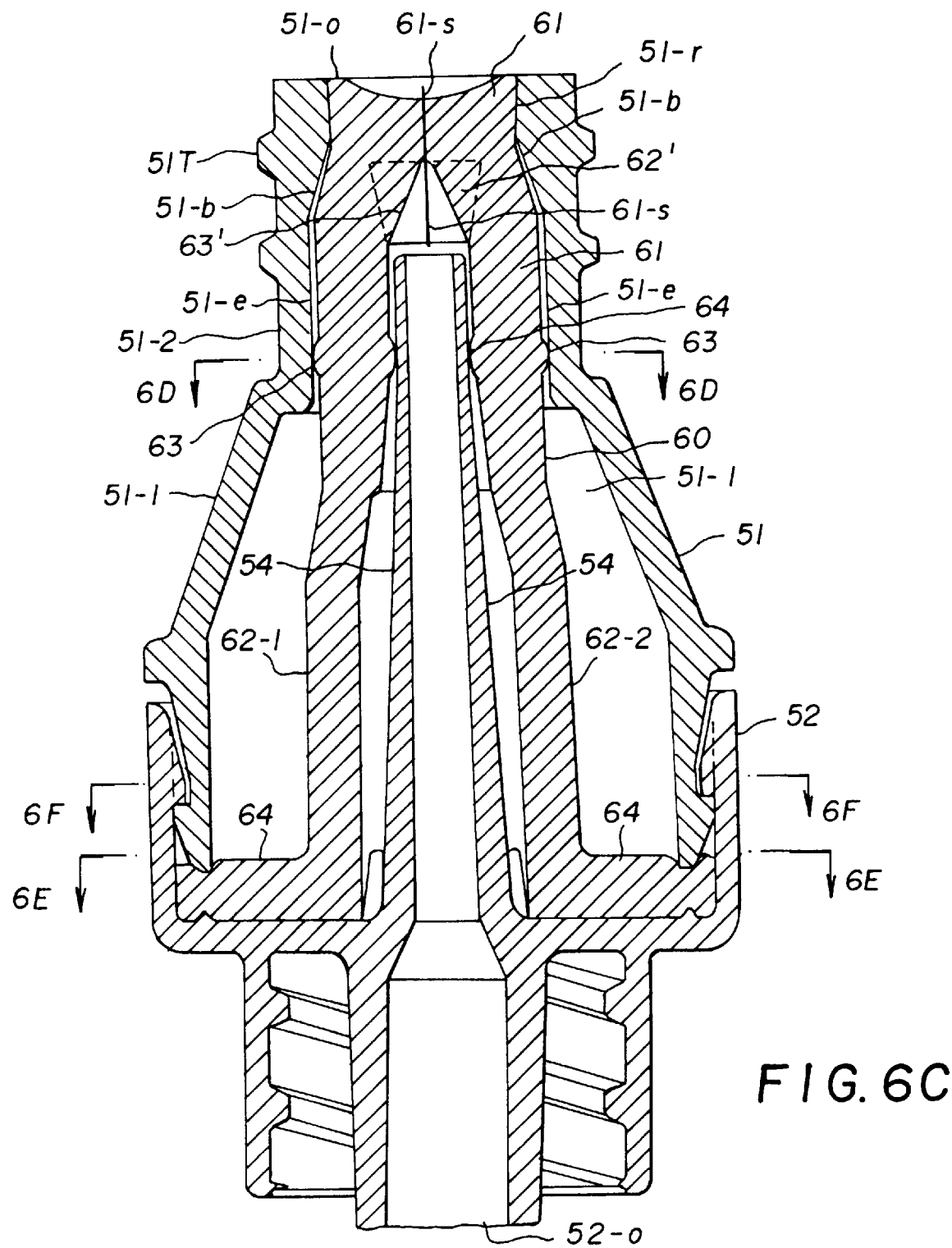
FIG. 6C is an enlarged sectional view of the flow-control valve of FIG. 6A in its closed valve position.
Figure 6E:
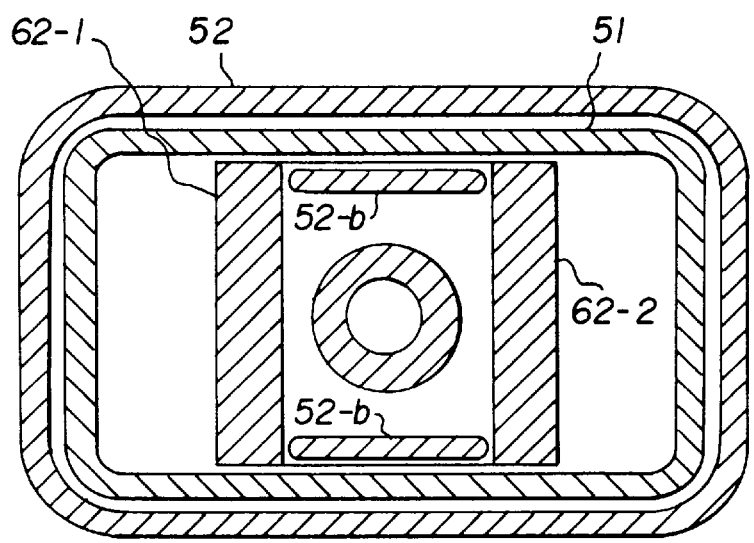
FIG. 6E is a sectional view of the flow-control valve of FIG. 6C taken along the lines A—A.

In the flow control device 50, the movable plug 60, together with the head 61 and the flexible body 62, extends between the inlet opening 51-*o* and the outlet opening 52-*o*. The flexible body 62 is expandable laterally with respect to the vertical axis A of the outlet channel 52-*o* in order to create spring pressure during opening and closing of the slit 61-*s*. Consequently, the upper or inlet housing 51 has an enlarged expansion chamber 51-1 as indicated in FIG. 6C. In addition, the housing 51 has a neck 51-2 with exterior Luer threads 51-*t* and a tapered bore 51-*b* beyond an interior cylindrical rim 51-*r*. Extending from the tapered bore 51-*b* is an elliptical or oval bore 51-*e* which, in turn, extends to the expansion chamber 51-1.

An elliptical or oval-shaped O-ring 63 of the plug 60 engages the elliptical or oval bore 51-*e*, and the oval-shaped head 61 seals the inlet rim 51-*r* by being compressed against its circular interior. The head 61 remains in sealing contact with the tapered bore 51-*b* of the neck 51-2, and then with the wall 51-*e*, as the plug 60 is depressed.

However, during movement of the plug 60 along the taper of the bore 51-*b*, the head 61 is depressed along an internal cannula 54 that extends upwardly from the base 52-*b* of the outlet housing 52 and the slit 61-*s* opens as shown in the fashion discussed above for the embodiment of FIGS. 2D and 2E.

Within the expansion chamber 51-1 legs of the body 62 are spaced from the chamber walls prior to depressing the seal plug for fluid flow as shown in FIG. 6C.

As in the prior embodiment of FIGS. 1B, 2C, 2D, 2E, 4A and 4C, the head 61 of the plug 60 has its upper slit 61-*s* within the spherical or oval concave depression 61-*d*, so that when a Luer tip is threaded on the neck 51-2 it seals circumferentially as before. The spherical or oval concavity 61-*d* on the top of the resilient seal plug 60 improves opening of the slit 61-*s* at the top of the seal plug head 61. It also helps to eliminate plug extrusion during valve activation by a Luer fitting or a syringe Luer outlet. The expansion of the head 61 also seals the neck 51-2 during valve operation.

The elliptical or oval shape of the resilient seal plug head 61 improves sealing pressure on the slit 61-*s* without the need for high compression. This configuration also allows high internal pressure, or low internal vacuum, without leakage and also achieves a desirably fast return of the seal plug head 61 to its sealing position within the rim 51-*r*, since there is reduced head compression of the seal plug.

The elliptical or oval shape of the internal neck 51-2 of the housing 51 below the Luer lock area further improves the performance of the primary seal. The internal elliptical or oval shape of the neck 51-2 corresponds to that of the seal plug head 61 when the cannula 54 moves through the resilient seal plug head along the slit 21-*s*. This is accomplished during valve opening because of pressure applied to the head 61 by a device such the Luer fitting 31 shown in FIG. 2D. The elliptical or oval shape of the internal neck 51-2 of the housing 51 additionally avoids a high degree of compression on the exterior wall of the internal blunt cannula 54. As a result, there is reduced interference that ensures a fluid seal at the elliptical interior of the neck 51-2 as well, as in the tapered region 51-*b* above the elliptical interior.

This reduction in interference permits a fast return of the head 61 of the seal plug 60 to its sealing position when a Luer fitting, or similar device, is removed following completion of valve activation.

In addition, the elliptical or oval shape of the O-ring 63 provides reduced interference in the neck region 51-2 of the housing 51 for a secondary seal which is desirable during the period of time that the valve 50 is in a fluid line, such as that of a IV set or vascular access system, and there is no activation with a Luer fitting or similar device. During this period, it is possible to have a high internal fluid pressure and the further seal of the circular O-ring 64 backs the pressure and avoids an internal pressure leak at the interface of the blunt cannula 54 and the internal circular O-ring seal 64.

In effect the control is by plug 60 with its upper head portion 61 sealing the inlet 51-*o*, and walls straddling the outlet cannula 54. The walls are extended legs 62-1 and 62-2 which are bowed and flexed or buckled under pressure in the axial direction of the outlet channel 52-*o*. They extend from below the head and neck 61 sealing the inlet 51-*o* to the base 52-*b* of the lower body 52 encircling the outlet channel cannula 54.

Figure 7A:
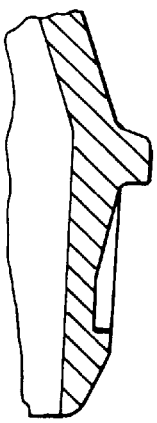
FIG. 7A shows a housing lock detail for the valve of FIGS. 6A and 6C.
Figure 6F:
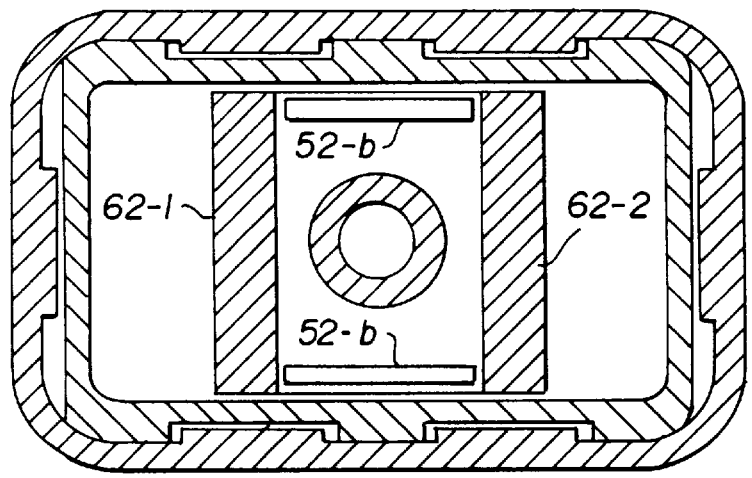
FIG. 6F is a sectional view of the flow-control valve of FIG. 6C taken along the lines B—B.
Figure 7B:
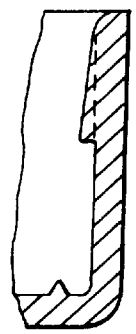
FIG. 7B shows a cap lock detail for the valve of FIGS. 6A and 6C.

The full scale side view of the valve 50 in FIG. 5A is similar that of FIG. 1A. However, the full scale side view of FIG. 6A differs from that of FIG. 2A by having tapered cap walls instead of the bowed walls of FIG. 2A. In addition, the cap 51 is affixed to the base 52 by a snap-lock mechanism illustrated in FIGS. 7A and 7B to facilitate assembly of the valve 50.

This lock mechanism is less expensive to produce than ultrasonic joining, and, as shown in FIG. 6C, the rectangular base 64 of the flexible seal 60 is interlocked in a hermetic seal condition by the joining of inlet housing 51 and outlet housing 52

In addition, the valve 50 does not need the cam interface 30 illustrated in FIGS. 2C through 2D and 3A through 3D. Instead, the plug 60, as shown in FIG. 5B, include a reverse taper interior 62', which transcends to an alternate taper interior 63' as shown in FIG. 6C.

In FIGS. 1A through 2D, the component elements 13 and 14 are joined, for example, by ultrasonic welding, as contrasted with the locking together by snap action in FIGS. 5A through 6C. The valves of the invention promote sterility by providing ease of accessibility. Prior art valves with recessed stoppers allow antimicrobial agents to accumulate in puddles on the tops of stoppers. Particulate matter may also collect on recessed tops.

An important aspect of the invention is that the slit extending through the movable seal or head of the plug is closable by pressure applied non-uniformly to head. Such pressure is applied principally at positions on opposite sides of the slit. In some case the closure pressure for the oval head is applied solely at opposite sides of the slit. In general, the head of the plug of the invention is configured to have pressure applied primarily opposite the slit during a seal transition from, for example, an oval interior to a round opening.

It will appreciated that there are numerous other transitions in which sealing pressure is applied non-uniformly to the head of the plug.

It also will be understood that the foregoing embodiments are illustrative only and that modifications and adaptations of the invention may be made without departing from its spirit and scope as defined in the appended claims.

What is claimed:

1. A method of controlling fluid flow which comprises the steps of:
    (1) sealing an inlet of a housing extending to a neck by a movable oval flexible stopper having a slit opening which compresses into said inlet to seal the slit opening of said stopper; and
    (2) further sealing said movable means in relation to said housing by an oval protuberance on said stopper; and
    (3) depressing said stopper to open said slit opening and permit the flow of fluid therethrough.

2. The method of claim 1 further including the steps of:
    (1) depressing said stopper by applying the tip of a Luer taper thereto; to cause the expansion of said stopper into a region containing a side wall and open the closed slit opening therein to permit the passage of fluid therethrough;
    (2) wiping said side wall of the region into which said stopper is expanded during the depression thereof and following the return of said stopper to its equilibrium position;
    (3) causing said fluid to flow through a closed channel to an outlet for said fluid;
    (4) causing said closed channel to move into said outlet.

3. The method of claim 2 wherein said closed channel is spring loaded to cause the return of said stopper to its equilibrium and sealed position when pressure is removed therefrom.

4. A flow control device comprising an inlet, having an interior circular rim, for the flow of fluid;
    an outlet connected to said inlet and disposed having an axis with respect thereto to serve as a conduit for flow into said inlet; and
    means moveable to said circular rim for sealing said inlet and having a neck extending from an outer surface within a housing of said inlet, said neck including an oval ring to provide a further seal of said moveable means in relation to said housing.

5. A flow control device comprising
    an inlet, having an interior circular rim, for the flow of fluid;
    an outlet connected to said inlet and disposed having an axis with respect thereto to serve as a conduit for flow into said inlet; and
    means moveable to said circular rim for sealing said inlet and having a flexible body of rectangular cross-section extending from a head portion thereof and spaced therefrom, including a channel extending to said outlet for permitting flow through said head to said outlet when said inlet is unsealed.

6. Apparatus as defined in claim 5 further including means for permitting the activation of said means movable by a member external to the flow control device, wherein said means movable terminates in said head sealing said inlet and which can be depressed therefrom by the external member.

7. A flow control device comprising
    an inlet, having an interior circular rim, for the flow of fluid;
    an outlet connected to said inlet and disposed having an axis with respect thereto to serve as a conduit for flow into said inlet; and
    compressible means having a slit and movable to said circular rim for sealing said inlet;
    wherein said compressible means has an upper surface with a spherical depression and includes an internal member which acts against said compressible means when depressed against said member;
    whereby the opening of said slit in said compressible means is facilitated and extrusion of said compressible means is reduced during operation.

8. A flow control device in accordance with claim 7 wherein said compressible means is elliptical to enhance sealing pressure without the need for excess compression, thus facilitating a return of said moveable means from an unsealed to a sealed position.

9. A flow control device in accordance with claim 7 wherein said inlet has a neck below its outer surface with said circular rim having an oval configuration to facilitate accommodation of said moveable means.

10. A flow control device in accordance with claim 7 wherein a cam interface is included within said moveable means and engageable by said member when said moveable means is depressed.

11. A flow control device in accordance with claim 7 wherein said moveable means has a stationary interior cam surface for facilitating the movement of an internal member within said moveable means during the depression thereof.

12. A flow control device in accordance with claim 7 wherein said inlet extends to a first body portion containing said moveable means;
    said outlet extends to a second body portion containing said moveable means; and
    said first body portion is locked to said second body portion.

13. A flow control device in accordance with claim 7 wherein said moveable means has a flexible body extending from a head portion thereof and includes a bore member extending to said outlet for permitting flow through said head portion to said outlet when said inlet is unsealed.

14. A flow control device in accordance with claim 13 wherein said inlet extends to a bore member which is in engagement with the head portion of said movable means and is spaced from the flexible body portion thereof, with said slit being opened when said head is moved along said bore member.

15. Apparatus as defined in claim 7 wherein said compressible member includes an oval head with a slit therein extending to a circular interior passageway.

16. A flow control device as defined in claim 7 comprising
    an internal member for acting against said moveable means when depressed against said member; and a cam interface is included within said moveable means and engageable by said member when said moveable means is depressed.

17. A flow control device as defined in claim 16 comprising said cam interface fabricated of a material which has a greater hardness than the material of said moveable means.

* * * * *